US006013261A

United States Patent [19]

Sonoda et al.

[11] Patent Number: 6,013,261

[45] **Date of Patent: *Jan. 11, 2000**

[54] RECOMBINANT MAREK'S DISEASE VIRUS (MDV) AND VACCINE

[75] Inventors: Kengo Sonoda; Masashi Sakaguchi; Kazuo Matsuo; Fukusaburo Hamada, all of Kumamoto, Japan

[73] Assignee: Juridical Foundation The Chemo-Sero-Therapeutic Research Institute, Kumamoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,660

[22] PCT Filed: May 28, 1996

[86] PCT No.: PCT/JP96/01428

§ 371 Date: Jan. 30, 1997

§ 102(e) Date: Jan. 30, 1997

[87] PCT Pub. No.: WO96/38565

PCT Pub. Date: Dec. 5, 1996

[30] Foreign Application Priority Data

Jun. 2, 1995 [JP] Japan .................................... 7-160106

[51] Int. Cl.$^7$ ......................... A61K 39/12; A61K 39/245

[52] U.S. Cl. .................................... 424/199.1; 424/229.1; 424/214.1; 424/816; 424/93.2; 435/69.3; 435/320.1; 536/23.72; 536/24.1

[58] Field of Search ............................. 424/199.1, 229.1, 424/214.1, 816, 93.2; 435/69.3, 320.1, 172.3; 536/23.72, 24.1

[56] References Cited

U.S. PATENT DOCUMENTS

| | | | |
|---|---|---|---|
| 5,171,677 | 12/1992 | Sakaguchi et al. | 435/91.1 |
| 5,558,860 | 9/1996 | Ross et al. | 424/93.2 |
| 5,659,153 | 8/1997 | Ishikawa et al. | 424/229.1 |

FOREIGN PATENT DOCUMENTS

| | | | |
|---|---|---|---|
| 6-022757 | 2/1994 | Japan . | |
| 90/02803 | 3/1990 | WIPO | C12N 15/38 |

OTHER PUBLICATIONS

Ross et al. (1) J. Gen. Virol. 74: 371–377, 1993.

Haynes et al. Science 260: 1279–1286, 1993.

"Proceedings 19th World's Poultry Congress", vol. 1, pp. 332–335, Amsterdam, Sep. 19–24, 1992.

Sakaguchi et al., "Construction of Recombinant Marek's Disease Virus Type 1 (MDV1) Expressing the *Escherichia coli* LacZ Gene as a Possible Live Vaccine Vector: The US10 Gene of MDV1 as a Stable Insertion Site", Vaccine, vol. 12, No. 10, pp. 953–957, 1994.

Sonoda et al., "Protection of Convential Chickens Against Marek's Disease and Newcastle Disease by MDV1 Recombinants", Current Developments in the Molecular Biology of Marek's Disease Virus Workshop, p. 23, 1995.

Eberle et al., "Topological Distribution of Virus–Specific and Cross–Reactive Antigenic Determinants on the gB Glycoprotein of the Herpes Simplex Viruses", Journal of Medical Virology, vol. 27, pp. 309–316, 1989.

Desrosiers et al., "Synthesis of Bovine Growth Hormone in Primates by Using a Herpesvirus Vector", Molecular and Cellular Biology, vol. 5, No. 10, pp. 2796–2803, Oct. 1985.

Glazenburg et al., "Construction and Properties of Pseudorabies Virus Recombinants with Altered Control of Immediate–Early Gene Expression", Journal of Virology, vol. 69, No. 1, pp. 189–197, Jan., 1995.

Federoff et al., "Expression of Nerve Growth Factor In Vivo From a Defective Herpes Simplex Virus 1 Vector Prevents Effects of Axotomy on Sympathetic Ganglia", Proc. Natl. Acad. Sci. USA, vol. 89, pp. 1636–1640, Mar. 1992.

Bzik et al., "The Nucleotide Sequence of the gB Glycoprotein Gene of HSV–2 and Comparison with the Corresponding Gene of HSV–1", Virology 155, pp. 322–333, 1986.

Lowe et al., "Varicella–Zoster Virus as a Live Vector for the Expression of Foreign Genes", Proc. Natl. Acad. Sci. USA, vol. 84, pp. 3896–3900, Jun., 1987.

Telford et al., "The DNA Sequence of Equine Herpesvirus–1", Virology, 189, pp. 304–316, 1992.

Whitbeck et al., "Comparison of the Bovine Herpesvirus 1 gI Gene and the Herpes Simplex Type 1 gB Gene", Journal of Virology, vol. 62, No. 9, pp. 3319–3327, Sep., 1988.

Hammerschmidt et al., "Conservation of a Gene Cluster Including Glycoprotein B in Bovine Herpesvirus Type 2 (BHV–2) and Herpes Simplex Virus Type 1 (HSV–1)", Virology 165, pp. 388–405, 1988.

Spaete et al., "Insertion and Deletion Mutagensis of the Human Cytomegalovirus Genome", Proc. Natl. Acad. Sci. USA, vol. 84, pp. 7213–7217, Oct. 1987.

Sondermeijer et al., "Avian Herpesvirus as a Live Viral Vector for the Expression of Heterologous Antigens", Vaccine, vol. 11, issue 3, pp. 349–358, 1993.

Chee et al., "Analysis of the Protein–Coding Content of the Sequence of Human Cytomegalovirus Strain AD169", Current Topics in Microbiology 154 and Immunlogy, vol. 154, pp. 126–169, 1990.

Ellinger et al., "The Glycoprotein B Homologue of Human Herpesvirus 6", Journal of General Virology, vol. 74, pp. 495–500, 1993.

(List continued on next page.)

*Primary Examiner*—Mary E. Mosher
*Assistant Examiner*—Ali R. Salimi
*Attorney, Agent, or Firm*—Browdy and Neimark

[57] ABSTRACT

A recombinant herpes virus is provided which efficiently expresses an exogenous protein of interest in an inoculated animal host to thereby endow the host with excellent immunization. A recombinant herpes virus which incorporates an exogenous gene expression cassette in which a herpes virus-derived gB gene (a gene homologous to herpes simplex virus gB gene) promoter is used as a promoter for expression of an exogenous gene.

8 Claims, 7 Drawing Sheets

OTHER PUBLICATIONS

Davison et al., "Genetic Relations Between Varicella–Zoster Virus and Epstein–Barr Virus", J. Gen. Virol., vol. 68, pp. 1067–1079, 1987.

Sakaguchi et al., "Sequence Determination and Genetic Content of an 8.9–kb Restriction Fragment in the Short Unique Region and the Internal Inverted Repeat of Marek's Disease Virus Type 1 DNA", Virus Genes 6:4, pp. 365–378, 1992.

Buckmaster et al., "Gene Sequence and Mapping Data From Marek's Disease Virus and Herpesvirus of Turkeys: Implications For Herpesvirus Classification", J. Gen. Virol., vol. 69, pp. 2033–2042, 1988.

Ross et al., "Nucleotide Sequence and Characterization of the Marek's Disease Virus and Homologue of Glycoprotein B of Herpes Simplex Virus", J. Gen. Virol., vol. 70, pp. 1789–1804, 1989.

Umino et al., "Protective Effect of Monoclonal Antibodies to Newcastle Disease Virus in Passive Immunization", Journal of General Virology, vol. 71, pp. 1199–1203, 1990.

"119th Japanese Society of Veterinary Science", p. 116, Mar. 31–Apr. 2, 1995.

"42nd Japan Virology Society", p. 166, 1994.

Fig. 2

```
-621  GATGTTTAGT CACGATAGAC ATCGGTTCGC CCCAGCCGTC GAATACAGCA

-571  TTATATTTTA GTGTTGAAAA TGTAGGGCTG CTTCCTCACT TAAAGGAGGA
                 PCR primer
-521  AATGGCTCGA TTCATGTTTC ATAGCAGTAG AAAAACAGAT TGGACCGTCA

-471  GTAAGTTTAG AGGGTTTTAT GACTTTAGCA CTATAGATAA TGTACTGCGG

-421  CCCATCGCAT GGCTTGGAAA TATATCAAAG AACTGATTTT TGCAACAGCT

-371  TTATTTTCTT CTGTATTTAA ATGTGGCGAA TTGCACATCT GTCGTGCCGA
                            primer for nucleotide sequence determination
-321  CAGTTTGCAG ATCAACAGCA ATGGAGACTA TGTATGGAAA AATGGAATAT

-271  ATATAACATA TGAAACCGAA TATCCACTTA TAATGATTCT GGGGTCAGAA
               /
             NdeI
-221  TCAAGCACTT CAGAAACGCA AAATATGACT GCAATTATTG ATACAGATGT

-171  TTTTTCGTTG CTTTATTCTA TTTTGCAGTA TATGGCCCCC GTTACGGCAG

-121  ATCAGGTGCG AGTAGAACAG ATTACCAACA GCCACGCCCC CATCTGACCC

 -71  GTCCAATATT CTTGTGTCCC TGCATTTTAT CTCACACAAT TTATGAACAG
              /                PCR primer
            SspI
                                 -1
 -21  CATCATTAAG ATCATCTCAC TATG
```

```
                    Xbal
SV40 late promoter  ↓    NDV-F cDNA
                ╱────────╲
               │          │── SV40 polyadenylation signal
HindIII ───────│          │
               │A4 pKA4BLF│
               │  9.5-Kbp │
               │        A4│
                ╲────────╱
```

Digestion with HindIII and XbaI
|
End Filling
|         ← Fragment P or N from gB promoter
Ligation
|
Fragment F, P or N from gB promoter

```
                ╱────────╲
               │          │── NDV-F cDNA
               │          │
               │A4        │── SV40 polyadenylation signal
               │          │
               │        A4│
                ╲────────╱
``` pKA4BPF or pKA4BNF

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 557 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

```
GATGTTTAGT CACGATAGAC ATCGGTTCGC CCCAGCCGTC GAATACAGCA TTATATTTTA     60
GTGTTGAAAA TGTAGGGCTG CTTCCTCACT TAAAGGAGGA AATGGCTCGA TTCATGTTTC    120
ATAGCAGTAG AAAAACAGAT TGGACCGTCA GTAAGTTTAG AGGGTTTTAT GACTTTAGCA    180
CTATAGATAA TGTACTGCGG CCCATCGCAT GGCTTGGAAA TATATCAAAG AACTGATTTT    240
TGCAACAGCT TTATTTTCTT CTGTATTTAA ATGTGGCGAA TTGCACATCT GTCGTGCCGA    300
CAGTTTGCAG ATCAACAGCA ATGGAGACTA TGTATGGAAA AATGGAATAT ATATAACATA    360
TGAAACCGAA TATCCACTTA TAATGATTCT GGGGTCAGAA TCAAGCACTT CAGAAACGCA    420
AAATATGACT GCAATTATTG ATACAGATGT TTTTTCGTTG CTTTATTCTA TTTTGCAGTA    480
TATGGCCCCC GTTACGGCAG ATCAGGTGCG AGTAGAACAG ATTACCAACA GCCACGCCCC    540
CATCTGACCC GTCCAAT                                                   557
```

(2) INFORMATION FOR SEQ ID NO:2:

(i) SEQUENCE CHARACTERISTICS:
(A) LENGTH: 624 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

```
GATGTTTAGT CACGATAGAC ATCGGTTCGC CCCAGCCGTC GAATACAGCA TTATATTTTA     60
GTGTTGAAAA TGTAGGGCTG CTTCCTCACT TAAAGGAGGA AATGGCTCGA TTCATGTTTC    120
ATAGCAGTAG AAAAACAGAT TGGACCGTCA GTAAGTTTAG AGGGTTTTAT GACTTTAGCA    180
CTATAGATAA TGTACTGCGG CCCATCGCAT GGCTTGGAAA TATATCAAAG AACTGATTTT    240
TGCAACAGCT TTATTTTCTT CTGTATTTAA ATGTGGCGAA TTGCACATCT GTCGTGCCGA    300
CAGTTTGCAG ATCAACAGCA ATGGAGACTA TGTATGGAAA AATGGAATAT ATATAACATA    360
TGAAACCGAA TATCCACTTA TAATGATTCT GGGGTCAGAA TCAAGCACTT CAGAAACGCA    420
AAATATGACT GCAATTATTG ATACAGATGT TTTTTCGTTG CTTTATTCTA TTTTGCAGTA    480
TATGGCCCCC GTTACGGCAG ATCAGGTGCG AGTAGAACAG ATTACCAACA GCCACGCCCC    540
CATCTGACCC GTCCAATATT CTTGTGTCCC TGCATTTTAT CTCACACAAT TTATGAACAG    600
CATCATTAAG ATCATCTCAC TATG                                           624
```

(2) INFORMATION FOR SEQ ID NO:3:

(i) SEQUENCE CHARACTERISTICS:
(A) LENGTH: 30 base pairs

-continued

```
        (B) TYPE: nucleic acid
        (C) STRANDEDNESS: single
        (D) TOPOLOGY: linear

   (ii) MOLECULE TYPE: cDNA

   (xi) SEQUENCE DESCRIPTION: SEQ ID NO:3:

GGAATTCCGT GTTGAAAATG TAGGGCTGCT                                  30


(2) INFORMATION FOR SEQ ID NO:4:

    (i) SEQUENCE CHARACTERISTICS:
        (A) LENGTH: 29 base pairs
        (B) TYPE: nucleic acid
        (C) STRANDEDNESS: single
        (D) TOPOLOGY: linear

   (ii) MOLECULE TYPE: cDNA

   (xi) SEQUENCE DESCRIPTION: SEQ ID NO:4:

GGAATTCCTG TGAGATAAAA TGCAGGGAC                                   29
```

RECOMBINANT MAREK'S DISEASE VIRUS (MDV) AND VACCINE

This is a rule 371 application based on the priority date of PCT/JP/96/01428 filed May 28, 1996.

TECHNICAL FIELD OF THE INVENTION

The present invention relates to a novel recombinant virus which can express an exogenous gene in an animal cell or in an animal body and can persistently infect even in the presence of a maternal antibody to continue antigen stimulation for a long period of time while escaping from challenge of the host immune system, thereby providing a vaccine which is effective even for conventional animals having a maternal antibody. The present invention also relates to a polyvalent live vaccine for animals using said recombinant virus. The present invention further relates to a recombinant virus vector which can be used as a drug delivery system (DDS) for production of physiologically active substances such as hormones or cytokines within the living body.

BACKGROUND OF THE INVENTION

Virus vector has widely been studied for efficiency of vaccination and for use as a gene introduction system into the living body. Particularly in the poultry industry, a study for application of poxviruses, especially fowlpox virus, has made a rapid progress. Under the circumstances, in order to develop a more efficient vector, the present inventors have investigated to make a vector from Marek's disease virus type 1 (hereinafter also referred to as "MDV1"), a kind of avian herpes viruses, and have reported many results thereof. For example, the present inventors have investigated more than 20 sites on the MDV1 genome, and as a result, have identified US10 gene as an insertion site for an exogenous gene which can stably retain an exogenous gene but does not impair the vaccine effects against Marek's disease [Japanese patent application No. 4-205933 (Japanese patent publication No. 6-22757); 4th International Symposium on Marek's Disease (1992), Amsterdam; Vaccine 1994 Vol. 12, 953–957]. A recombinant virus which incorporates F protein gene of Newcastle disease virus into the US10 gene exhibited sufficient effects as a vaccine in SPF chickens, said effects being persistent over at least 24 weeks after inoculation (4th International Symposium on Marek's Disease (1992), Amsterdam). This recombinant virus has been proved to show protective effects against both Marek's disease and Newcastle disease even in chickens having maternal antibodies but the protective effects were somewhat lowered than in SPF chickens. That is, this recombinant virus showed efficiently 100% protective effects against Newcastle disease in SPF chickens whereas it showed somewhat lowered effects, i.e. 70 to 90% level, in field chickens having maternal antibodies (Current Developments in the Molecular Biology of Marek's Disease Virus Workshop, 1995, Florida). Such a decrease in the effects was supposedly due to suppression of in vivo growth of the recombinant virus by maternal antibodies against Newcastle disease and Marek's disease when field chickens are immunized with the recombinant virus.

DISCLOSURE OF THE INVENTION

As mentioned above, when a live vaccine comprising a recombinant virus is inoculated into an animal having maternal antibodies, a problem arises that said virus is eliminated or viral growth is inhibited by the host immune system such as maternal antibodies. Thus, an improved recombinant virus is desired which retains the properties of a live vaccine and can continuously provide antigen stimulation for a long period of time while escaping from the challenge of the immune system.

In order to solve the above-mentioned problem, the present inventors have noted promoters derived from MDV1 and have cloned several putative promoter genes from Marek's disease virus (hereinafter also referred to as "MDV") genome. Using these promoter genes, the present inventors have conducted an experiment for expression of an exogenous gene in a recombinant virus comprising said genes. As a result, it was found, that among several promoter genes which the present inventors have cloned, a promoter from glycoprotein B (hereinafter referred to as "gB") gene, a gene homologous to herpes simplex virus gB gene, exhibited particularly excellent effects in expression of an exogenous gene (e.g. Newcastle disease virus F protein (hereinafter also referred to as "NDV-F")), and in addition, exerted much excellent immunization effects in animals than expected. That is, an amount of F protein expressed with this promoter in culture cells was apparently lower than that of a recombinant virus with conventional promoters (e.g. SV40 promoter), but nevertheless a quite high immunogenicity in animals (chickens) was observed contrary to expectations, i.e. a recombinant virus with this promoter exhibited more protective effects against Newcastle disease than those of the conventional recombinant viruses and steadily exhibited the protective effects of more than 95% even when it is used for immunization of field chickens having a maternal antibody, effective immunization of animals with a maternal antibody having been a pending problem.

BRIEF DESCRIPTION OF THE DRAWINGS

FIG. 2 shows a nucleotide sequence upstream of gB gene as well as each position of primers used for nucleotide sequence determination and PCR primers, SEQ ID NO:2.

BEST MODE FOR CARRYING OUT THE INVENTION

Figure 1:
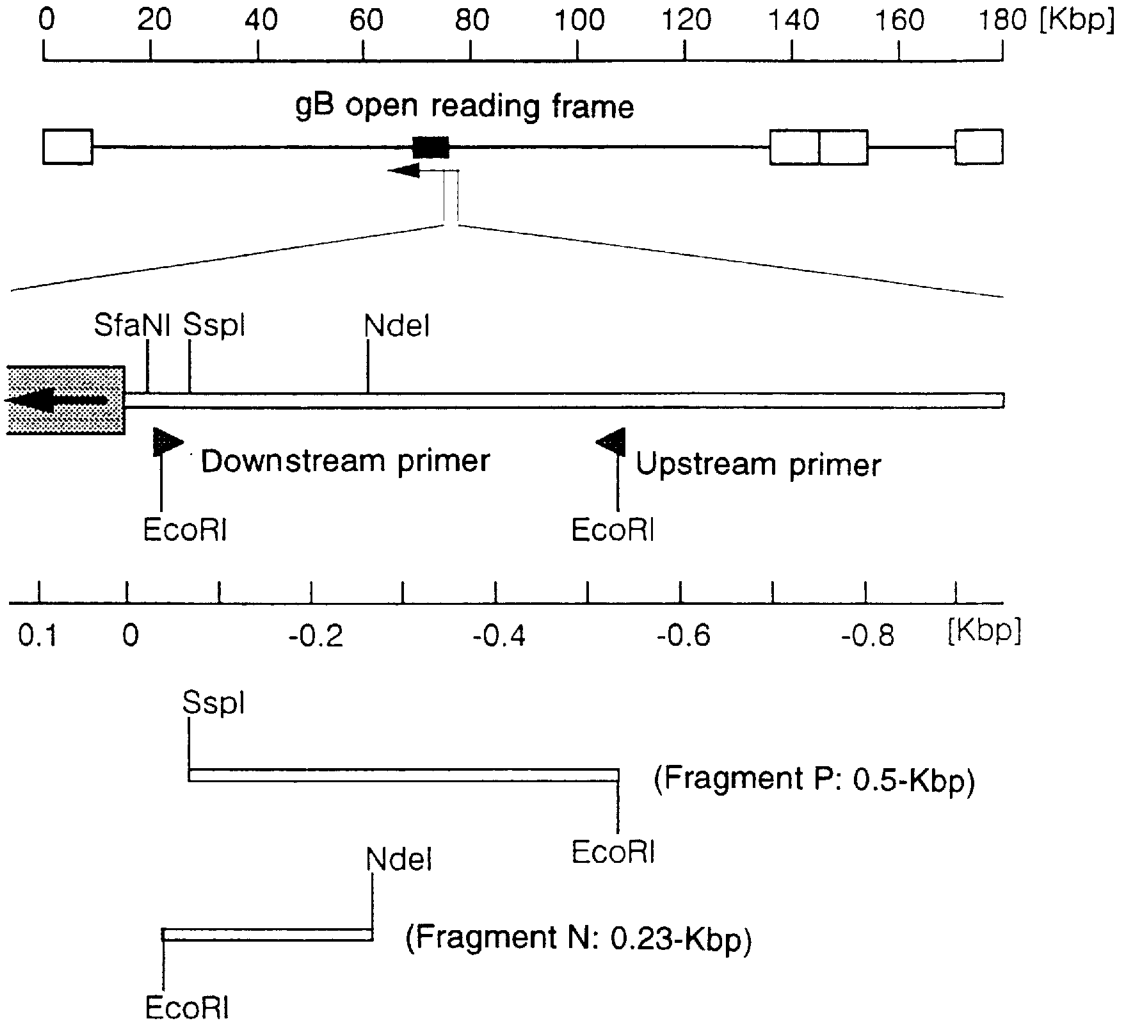
FIG. 1 is a schematic illustration of cloned putative gB promoter fragments.

In view of excellent protective effects obtained in the immunization experiment as mentioned above, herpes virus-derived gB promoter used in the present invention supposedly have the characteristics as mentioned hereinbelow.

That is, Marek's disease live vaccine viruses persistently infect within the body of chicken in spite of the presence of neutralizing antibodies in blood thereby to induce a high antibody titer against MDVs. Although a mechanism is unknown where the virus circumvents the host immune system to continue to induce an antigen stimulation, one possibility might be that a tissue where latent infection of the virus is present is distinct from a tissue where an antigen (e.g. gB) is expressed. That is, it is estimated that, in a tissue where latent infection of Marek's disease virus is present, a target antigen for the immune system is not expressed, and as a result, the virus can escape from the guard of the host immune system. Such latent virus is supposedly often activated and stimulates the immune system possibly by infecting to another tissue where it expresses a viral antigen, thereby a high production of an antibody being induced.

gB, an expression of which is intrinsically controlled by gB gene promoter, the promoter successfully cloned in the present invention, is a glycoprotein which induces neutralizing antibody production against the virus. It is estimated that although production of an antibody against the gB (i.e. a neutralizing antibody) is induced in MDV-infected chickens, MDVs escape from the neutralizing antibody and infect persistently to cause an antigen stimulation to thereby induce a high antibody titer. That is, it was estimated that gB promoter expresses gB in specific cells but not in those cells where MDVs are latent, and as a result, MDVs can persistently infect while escaping from the host immune system. Accordingly, by using the gB promoter for expression of Newcastle disease virus F protein, the expression of F protein is similarly controlled by the gB promoter, and as a result, a recombinant virus acquired properties of persistent infection while escaping from the challenge of the host immune system.

On the contrary, for SV40-derived promoter incorporated into various recombinant viruses, which the present inventors have hitherto constructed, although a promoter activity itself is well potent, the recombinant viruses express F protein even on the surface of those cells where latent infection might be possible, and as a result, the viruses are targeted by the immune host system and hence easily eliminated from within the living body, due to the absence of the control mechanism as mentioned above. Under the circumstances, especially in the presence of maternal antibodies, it was estimated that the recombinant viruses could not sufficiently propagate due to more rapid elimination by the immune system.

Other glycoproteins homologous to MDV-gB are well preserved in a number of herpes viruses and are considered to be an antigen responsible for protection from infection (R. Eberl et al., J. Med. Virol. 27: 309–316 (1989)). In view of this, for not only Marek's disease virus but also another herpes viruses used as a vector, the use of gB gene promoter was considered to be quite effective for efficient expression of an exogenous gene of interest and maintenance of the vaccine effect for a long period of time. In a preferable embodiment, an effective recombinant herpes virus is prepared by using a gB promoter gene from herpes virus (i.e. a gB promoter gene which is intrinsically contained in said herpes virus). Such herpes viruses include, in addition to MDV, herpesvirus saimiri [R. C. Desrosiers et al. Molecular and Cellular Biology 5, 2796–2803 (1994)]; Aujeszky's disease virus [K. L. Glazenburg et al., J. Virology, 69, 189–197 (1995)]; herpes simplex virus type 1 (hereinafter referred to as "HSV1") [H. J. Federoff et al., Proc. Natl. Acad. Sci. USA 59, 1636–1640 (1992)]; herpes simplex virus type 2 (hereinafter referred to as "HSV2") [J. B. David et al., Virology 155, 322–333 (1986)]; herpes zoster virus [R. S. Lowa et al., Proc. Natl. Acad. Sci. USA 84, 3896–3900 (1987)]; equine herpes virus type 1 [A. R. Elizabeth et al., Virology 189, 304–316 (1992)]; bovine herpes virus type 1 (hereinafter referred to as "BHV1") [J.C. Whitbeck et al., J. Virology 62, 3319–3327 (1988)]; bovine herpes virus type 2 (hereinafter referred to as "BHV2") [W. Hammerschmitdt et al., Virology 165, 388–405 (1988)]; feline herpes virus type 1 [R. S. Spaete et al., Proc. Natl. Acad. Sci. USA 84, 7213–7217 (1987); Naoaki Yokoyama et al., 119th Japan Veterinary Society, Brief Text, p116 (1995)]; turkey herpes virus (hereinafter referred to as "HVT") [P. J. Sondermeijer et al., Vaccine, 11, 349–358 (1993)]; human cytomegalovirus (hereinafter referred to as "HCMV") [J. K. McDougall, Cytomegaloviruses, Springer-Verlag, Berlin-Heidelberg]; human herpes virus type 6 (hereinafter referred to as "HHV6") [K. Ellinger et al., J. Gen. Virol. 74, 495–500 (1993)]; human herpes virus type 7 (hereinafter referred to as "HHV7") [Atsuko Haneda et al., 42th Japan Virology Society, Brief Text, p166 (1994)]; Epstein-Barr virus (hereinafter referred to as "EBV") [A. J. Davison et al., J. Gen. Virol. 68, 1067–1079 (1987)], and the like.

According to the present invention, in addition to the above-mentioned effects that an exogenous gene expression is controlled in host cells inoculated with the virus, there can also be obtained effects that the promoter gene fragments for expression of an exogenous gene are shorter than the conventional promoters such as SV40 promoter and thus, by the shortened portion, a longer structural gene (exogenous gene) for expression can suitably be incorporated into a plasmid so that construction of plasmid and a recombinant virus becomes easier.

The present invention is explained in more detail by referring to, by way of example, a recombinant virus in which MDV is employed as herpes virus.

The present inventors have cloned 5' site of the genes encoding gB, US10, US537 and US420 [Sakaguchi et al., Virus Gene 6, p365–378 (1992)] as a MDV-derived promoter and, using these gene fragments, have conducted an experiment for expression of an exogenous gene. As a result, the 5' fragment of gB gene among these promoters could successfully express the exogenous gene in culture cells and thus gB promoter was selected for further investigation as described below.

The gB gene's position on the MDV1 genome has been reported by Anne E. Buckmaster et al. [J. Gen. Virol. 69, p2033–2042 (1988)]. Thereafter, nucleotide sequences of gB gene and upstream thereof up to −360 bases have also been reported [L. J. N. Ross et al., J. Gen. Virol. 70, p1789–1804 (1989)]. However, there has yet been no report on the identification of a promoter region involved in expression of gB gene as well as activities thereof. Thus, the present inventors have firstly identified the promoter region for use in a recombinant virus.

First, referring to the nucleotide sequence reported by Ross et al. [J. Gen. Virol. 70, p1789–1804 (1989)], primers were designed and a further upstream nucleotide sequence was determined by the primer extension method.

Then, a 5' primer was designed within the determined region and a 3' primer just before the gB open reading frame (ORF), and about 500 nucleotides were amplified by PCR and cloned. Then, to the downstream of said nucleotides was ligated an F protein gene of NDV to construct an expression plasmid. Similarly, using only the 3' half of the nucleotides amplified by PCR, a plasmid for expression of the F protein gene was constructed and subjected to experiment.

For measuring promoter activities, the expression in culture cells was first confirmed. That is, the plasmids were introduced into chicken embryo fibroblasts (CEF) and the expression of F protein was detected by the fluorescent antibody method using a monoclonal antibody recognizing F protein. Then, recombinant viruses were constructed using each plasmid and F protein expression in each recombinant virus was confirmed. As a final experiment, each of the recombinant viruses was inoculated into chickens having maternal antibodies and immunogenicity thereof was compared. As a result, there was no difference between the recombinant viruses in an expressed amount of F protein in culture cells whereas immunogenicity after inoculation into chickens unexpectedly much differed. That is, it was found that the recombinant virus with the whole nucleotide sequence amplified by PCR showed extremely high immunogenicity while the recombinant virus comprising only the 3' half of the amplified sequence as a promoter exhibited extremely low immunogenicity.

Thus, as a gB promoter region for expression of an exogenous gene in a recombinant virus, not only up to about 200 to 300 nucleotides upstream of the translation initiation codon, commonly a minimum region as a promoter, but also further upstream region of from −262 nucleotide up to −561 nucleotide (cf. FIG. 2) containing a transcriptional control factor are critical. That is, it was shown that the minimum requisite sequence for promoter is contained within about the 3' half of the cloned sequence of around 500 nucleotides in view of the F protein expression in culture cells, but the transcriptional control region contained in the 5' half of the cloned sequence plays an important role in efficient expression within the living body of chickens.

A most preferable embodiment of such promoter gene fragment for use in an exogenous gene expression in the present invention is a gene fragment comprising a sequence of from nucleotide 61 to nucleotide 557 in SEQ ID NO:1 of the Sequence Listing. Since there are various subtypes of Marek's disease virus, a mutation might possibly occur within a portion of the gB promoter gene. For a sequence of gB promoter gene to be used in the present invention, in case of Marek's disease virus, any gB promoter sequence which is highly homologous to the above sequence in SEQ ID NO:1 may be used without any limitation for expression of an exogenous gene.

In addition to Marek's disease virus type 1, other herpes viruses have also structural proteins with a highly homologous amino acid sequence to that of gB protein, and thus, promoter sequences which control expression of these proteins may also be used for construction of the recombinant virus of the present invention.

An exogenous gene controlled by such gB promoters for incorporation into the genome of Marek's disease virus includes various genes encoding proteins of a possible vaccine antigen for various chicken diseases including viral diseases, bacterial diseases, parasitic disease, and the like. For example, for preparing a polyvalent vaccine for use in chickens, an exogenous gene to be incorporated includes a gene encoding Newcastle disease virus (NDV) antigen (e.g. genes encoding NDV-F protein or HN protein), a gene encoding a glycoprotein of avian infectious laryngotracheitis (ILTV), a gene encoding a viral structural protein of infectious bursal disease virus (IBDV), e.g. genes encoding VP2 or a whole of VP243, a gene encoding a spike protein of infectious bronchitis virus (IBV), a gene encoding HA protein of *Heamophilus paragallinarum*, a causative agent of infectious coryza, and the like. As an antigen to be used for prevention of viral diseases, since, in case of influenza virus, a nuclear protein (NP) has been shown to be a key antigen effective for prevention irrespective of serotype, a nuclear protein gene in another viruses is possibly a critical antigen gene for protection.

For expression of exogenous genes as mentioned above, an expression cassette is constructed using the gB promoter gene of the present invention and the cassette is incorporated into MDV to prepare a polyvalent vaccine with a single virus (recombinant MDV) since MDV itself functions as a vaccine against Marek's disease virus. As desired, a vaccine of more than 2 valencies can also be prepared, and a polyvalent vaccine of more than 3 valencies comprising only one kind of a recombinant virus can also be prepared by incorporating a plurality of different foreign gene expression cassettes into a single virus. Such vaccine can easily be prepared by utilizing the known prior art techniques.

The recombinant virus of the present invention may be inoculated into chickens of any week old. It should be noted that the most characteristic feature of the recombinant virus of the present invention is that it can effectively be inoculated into chickens having maternal antibodies like just after hatching. Furthermore, it is also possible to inoculate at the stage of developing eggs, most suitably at 17 to 18 days old embryo.

In addition to expression of the above-mentioned vaccine antigens, the recombinant virus of the present invention is also useful as a viral vector for expression of physiologically active proteins other than the vaccine antigens in inoculated animals. That is, since the recombinant herpes virus of the present invention is not a transient expression system but, when administered to animals, enables persistent infection while escaping from the immune system within the animal body, it is expected to be quite efficacious as a drug delivery system (DDS) for effectively producing an exogenous gene product within the living body.

The present invention is illustrated in more detail by means of the following Preparation and Examples.

[Preparation]

(1) Viral strain

Marek's disease virus type 1 CVI988 strain was used for cloning of gB promoter gene region and construction of a recombinant virus.

(2) Preparation of viral DNA

After inoculation of the virus into chicken embryo fibroblasts (CEFs), the infected cells were harvested when cytopathic effect (CPE) was intensely exhibited. The infected cells were suspended in 1%-SDS solution (0.1% Tris-HCl, pH 7.4, 1 mM EDTA, 1% Sarcocinate; manufactured by Wako Junyaku Kogyo K.K.) containing 0.1% Proteinase K (Boehlinger Mannheim) and the suspension was left to stand at 37° C. overnight. Then, the phenol treatment and the ethanol precipitation were conducted to recover DNAs, which were dissolved in a suitable amount of TE buffer (10 mM Tris-HCl, pH 8.0, 1 mM EDTA) to give a solution of viral DNAs.

(3) Cloning of viral DNA fragments

The thus prepared viral DNAs (5 μg) were digested with a restriction enzyme and fragments were separated by electrophoresis on 0.8% agarose gel. The DNA fragments were eluted from the gel by the electroelution method and recovered by the phenol treatment and the ethanol precipitation. The obtained fragments were inserted into a suitable plasmid vector (e.g. pUC119; Takarashuzo) with a ligation kit (Takarashuzo) and competent cells (e.g. JM109) were transformed with the vector to give transformant *E.coli*. Then, the transformant cells were grown on a circle grow medium (BIO101, INC.) containing 100 μg/ml ampicillin and thereafter the plasmids were collected from the cells by the alkaline method.

(4) Determination of nucleotide sequence

After cloning of the gene fragments into the multiple cloning site of pUC119, the plasmids were transduced into competent cells such as JM109. After the obtained transformants were grown on LB medium overnight, 30 μl of the transformants were infected with 60 μl of M13 phage ($10^9$ PFU/ml or more) and further grown by shaking culture overnight. After removing the cells by centrifugation, the phages were collected from supernatant and a single-stranded DNA (ssDNA) containing a nucleotide sequence of a desired gene fragment was prepared by the conventional procedure. A nucleotide sequence of the obtained ssDNA was determined with SEQUENASE Ver. 2.0 (Toyobo) in accordance with the protocol attached thereto.

(5) PCR

The viral DNA (0.1 μg) was dissolved in 1× Vent buffer (10 mM KCl, 20 mM Tris-HCl, pH 8.8, 10 mM $(NH_4)_2SO_4$, 2 mM $MgSO_4$) containing 100 pg/ml BSA and thereto were added 0.5 mM dNTP, each 100 pmmol of upstream and downstream primers and 1 μl Vent DNA polymerase (New England BioLabs). The reaction was conducted for 35 cycles, each cycle consisting of 95° C. for 1 minute, 55° C. for 1 minute and 72° C. for 1 minute.

(6) Fluorescent antibody (FA) method

CEF $10^6$ cells/well were seeded to a 6-well plate containing one cover glass (MATSUNAMI No.1 18×18) and cultured on Eagle medium with 5% FBS at 37° C. for 5 hours. After washing twice with a serum free Eagle medium, 1 ml of a serum free Eagle medium containing lipofectin 10 μg and the insertion plasmid 30 μg was added and the cells were cultured at 37° C. for 16 hours. After addition of 1 ml Eagle medium with 10% FBS and culture for 2 days, the cover glass was removed and the cells were fixed with acetone at room temperature for 20 minutes and then stored at −80° C. F protein expression in the recombinant viruses was confirmed by reaction with anti-NDV-F monoclonal antibody #313 [Y. Umino et al., J. Gen. Virol. 71, p1199 (1990)] diluted 20-fold with PBS(−) at 4° C. overnight and then by reaction with FITC-labeled anti-mouse IgG diluted 20-fold with PBS(−) at 37° C. for 2 hours, followed by washing and observation with a fluorescent microscope.

(7) Preparation of recombinant virus

After primary culture CEFs, cultured at 37° C. overnight, were harvested and washed with an EDTA-trypsin solution, they were suspended in Eagle-MEM (E-MEM: Nissui) supplemented with 5% bovine serum (BS) at a cell concentration of $2\times10^5$ cells/ml. A tissue culture flask manufactured by Falcon (No. 3028) was charged with 40 ml of the suspension and thereto was seeded about $8\times10^5$ CEF cells infected with Marek's disease viruses, followed by culture at 37° C. for 4 hours. Then, the cells were again harvested with a EDTA-trypsin solution and washed twice with PBS(−), of which $5\times10^6$ cells were transferred to a cuvette of Gene Pulser manufactured by Bio-Rad (Catalogue No. 165-2075) and thereto was added the insertion plasmids. Pulse was then applied in accordance with the attached protocol to introduce the insertion plasmids into the viral infected cells. Then, the cells were suspended in E-MEM (Nissui) 15 ml supplemented with 5% BS, transferred to a laboratory dish of 10 cm diameter (manufactured by Falcon; No.3003) and cultured at 37° C. The next day, the culture medium was removed together with those cells not being taken, and primary culture CEFs (second CEFs), which were separately cultured the previous day and suspended in E-MEM (Nissui) 15 ml supplemented with 5% BS at $5\times10^5$ cells/ml, were added and culture was continued at 37° C. for 4 to 7 days.

After washing the laboratory dish where plaques appeared with E-MEM medium, an isotonic solution containing the monoclonal antibody #313 was added thereto and the reaction was conducted at room temperature for 1 hour. After washing, peroxidase-labeled mouse antibody (Bio-Rad Code No. 172-1011) diluted 200-fold with an isotonic solution was added thereto and the reaction was further conducted at room temperature for 1 hour. After washing, thereto was added 0.1 M Tris buffer containing 5 mg of 3,3-diaminobenzidine tetrahydrochloride (DAB; Wako Junyaku Kogyo K.K., Code No. 343-00901) and 1.6 mg of hydrogen peroxide (Mitsubishi Gasu Kagaku K.K., containing 31% $H_2O_2$) per 10 ml and the reaction was carried out at room temperature for 10 to 60 minutes to stain the plaques of the recombinant virus. The plaques stained brown were enclosed with a penicillin cup and only the area within the cup was digested with a trypsin solution containing 0.1% EDTA to harvest cells infected with the recombinant virus, which were cultured with fresh CEFs for purification of the recombinant virus. After confirming that 100% of the viral plaques expressed F protein, ultrasonication was conducted twice to render the virus being cell-free in accordance with the procedures described in Japanese patent application No. 4-205933 (Japanese patent publication No. 6-22757) to complete purification of the recombinant virus.

(8) Southern hybridization

Using DIG-DNA Labeling Kit (Catalogue No. 150350) manufactured by Boehlinger Mannheim, probes were prepared and hybridization was conducted in accordance with the attached protocol.

A suitable amount of the recombinant virus DNA obtained above was electrophoresed on an agar gel, and after electrophoresis, it was transferred to Hybond N+ (Amersham Japan, Catalogue No. RPN.303B). Hybridization was carried out in accordance with the protocol. Then, using DIG-DNA Detection Kit (Catalogue No. 150350) manufactured by Boehlinger Mannheim, DNA of interest was detected in accordance with the attached protocol.

(9) Immunization Test

Babcock chickens of 1 day old were inoculated subcutaneously with $10^4$ PFU/chicken of the recombinant virus. Each group of chickens was bled periodically since 4 weeks after inoculation and a change of a titer of anti-F protein antibody induced by the recombinant virus was measured by ELISA. ELISA for measuring antibodies was employed wherein cells producing persistently F protein (mouse myeloma cells P3-X63-AG8.653 transformed with NDV-F gene under control of β-actin gene promoter) immobilized on a 96-well plate for tissue culture was used as an antigen as disclosed in detail in Japanese patent application No. 5-96727 (Japanese patent publication No. 6-289028).

On the other hand, in order to assess protective effects against infection with Newcastle disease virus, a half number of each group was challenged intramuscularly with a lethal dose of $10^4$ virulent NDV Sato strain at 6 weeks old and was observed for 2 weeks. As to protective effects against infection with Marek's disease virus type 1, intraperitoneal challenge with 500 PFU/chicken of very virulent MDV (vvMDV) RBIB (infected spleen cells) was made at 1 week old and chickens were observed until 10 weeks old. All survived chickens were subjected to necropsy to check the presence of tumoral lesion.

(10) Recovery of virus from the chicken body

After bleeding with a 1 ml heparin-sucked syringe, PBS (−) was added to make 4 ml, which was gently overlaid to Ficoll-Paque (Pharmacia) 3 ml in Conical Tube (Falcon, Catalogue No. 2099) and was centrifuged at 1500 rpm for 5 minutes (KUBOTA KN-30F). A middle layer comprising lymphocytes and monocytes (Buffy coat) was removed and, after being suspended in PBS(−) containing 0.1% EDTA, was again centrifuged at 1000 rpm for 5 minutes to collect lymphocytes and monocytes, which were inoculated to CEFs cultured for 4 hours (second CEFs) and CEFs were cultured and observed for 10 days. For those CEFs which exhibited no CPE of MDV, they were subcultured to the 3rd generation and then assessed.

EXAMPLE

Using by way of example a vector wherein a Marek's disease virus is used as a herpes virus, cloning of gB promoter region and construction of recombinant virus are illustrated hereinbelow for construction of recombinant live vaccine for chicken.

Example 1

Determination of nucleotide sequence upstream of qB gene

BamHI-I3 fragment comprising a nucleotide sequence of gB gene as described by Ross et al. [J. Gen. Virol. 70, p1789-1804 (1989)] was digested with restriction enzymes EcoRV and SspI and the obtained fragment of about 1.2 Kbp was subcloned into pUC119. As described in Preparation, a nucleotide sequence was determined for a region further upstream of gB gene using the plasmid. A nucleotide sequence of about 300 bp to upstream direction was first determined and then determination of a nucleotide sequence was made to downstream direction up to the SspI site so that a total of 557 bp nucleotide sequence was determined. The result is shown as SEQ ID NO: 1. A sequence from the nucleotide 558 to the translation initiation codon ATG (nucleotide 624) in SEQ ID NO: 2 is at the 3' site of the above 557 bp sequence and has been reported by Ross et al. (ibidem). The primer which the present inventors used for determination of nucleotide sequence corresponds to the nucleotides 275 to 291 in SEQ ID NO: 1.

Example 2

Cloning of qB gene promoter region by PCR

Primers were designed based on the nucleotide sequence obtained in Example 1 (cf. SEQ ID NO: 1) for an upstream primer or on the sequence reported by Ross et al. [J. Gen. Virol. 70, p1789-1804 (1989)] for a downstream primer. That is, an upstream primer was designed between the nucleotides 61 and 82 in SEQ ID NO: 1 and a downstream primer between the nucleotides 566 and 586. Each sequence of the primers are shown below.

Upstream

5'-GGAATTCCGTGTTGAAAATGTAGGGCTGCT-3' (SEQ ID NO:3)

Downstream

5'-GGAATTCCTGTGAGATAAAATGCAGGGAC-3' (SEQ ID NO:4)

PCR conditions were as follows: i.e. the viral DNA 0.1 $\mu$g was dissolved in 1× Vent buffer (10 mM KCl, 20 mM Tris-HCl, pH 8.8, 10 mM $(NH_4)_2SO_4$, 2 mM $MgSO_4$) containing 100 $\mu$g/ml BSA and to the solution were then added 0.5 mM dNTP, each 100 pmmol of the upstream and downstream primers and 1 $\mu$l Vent DNA polymerase (New England Biolabs). The reaction was conducted for 35 cycles, each cycle consisting of 95° C. for 1 minute, 55° C. for 1 minute and 72° C. for 1 minute. As a result, a DNA fragment of about 0.5 Kbp was successfully amplified. This DNA fragment was digested with EcoRI and SspI to give a DNA fragment of about 0.5 Kbp (hereinafter referred to as "fragment P", a nucleotide sequence of which corresponds to the nucleotides 61 to 557 in SEQ ID NO: 1) and with EcoRI and NdeI to give a DNA fragment of 230 bp (hereinafter referred to as "fragment N", a nucleotide sequence of which corresponds to the nucleotides 359 to 586 in SEQ ID NO: 2) as a gB gene promoter region (cf. FIGS. 1 and 2).

Example 3

Figure 3:
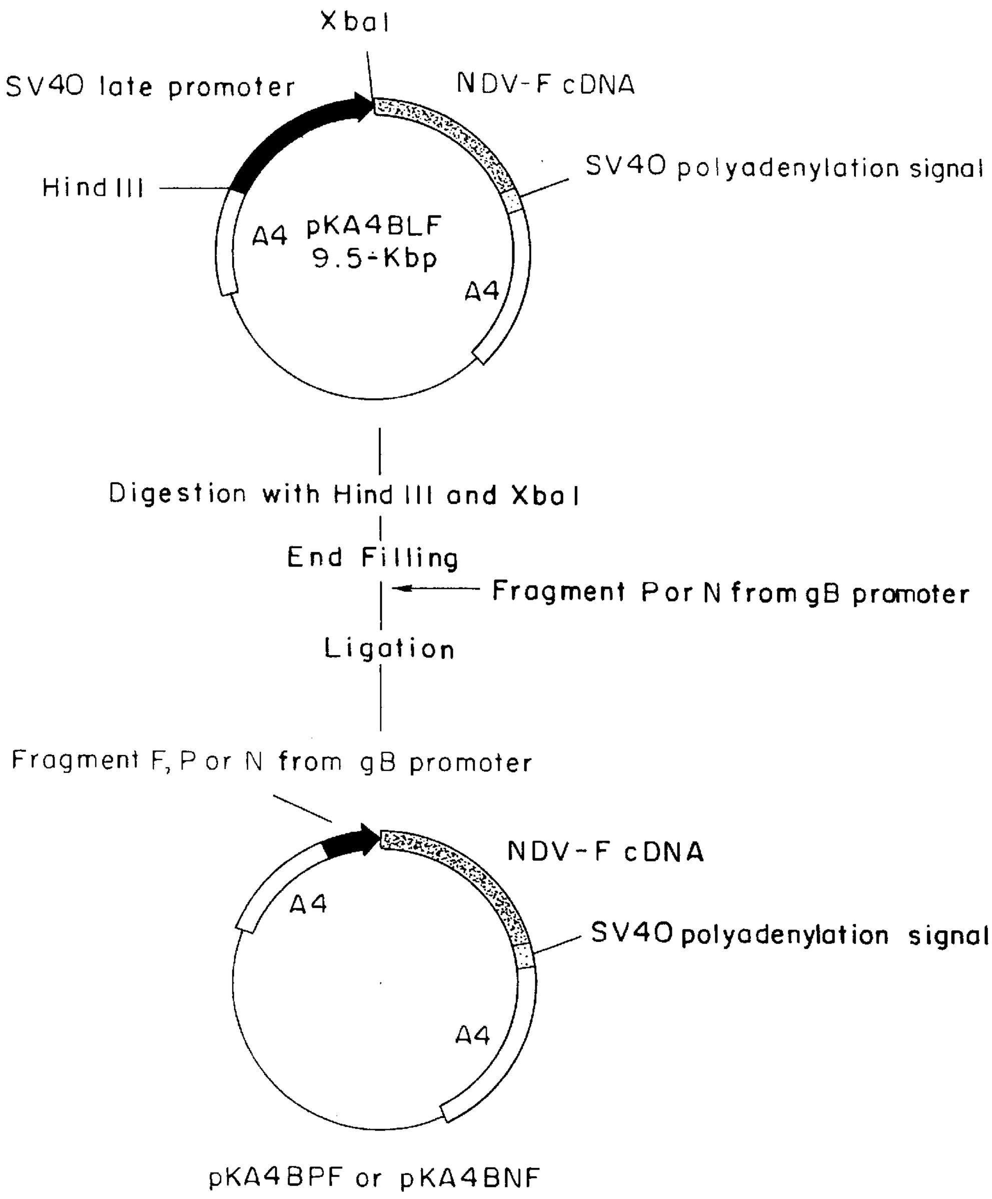
FIG. 3 shows construction of insertion vector plasmids (pKA4BPF and pKA4BNF) for expression of NDV-F protein with gB promoter.

Construction of insertion vector plasmid for expression of NDV-F protein via gB promoter After digesting insertion vector plasmid pKA4BLF (described in Japanese patent application No. 4-205933 (Japanese patent publication No. 6-22757)), which expresses NDV-F protein via SV40 late promoter, with restriction enzymes HindIII and XbaI, a DNA fragment of about 7.9 Kbp deprived of SV40 late promoter sequence was recovered by 0.8% agar gel electrophoresis. After this fragment was blunt-ended with Blunt End Ligation Kit (TaKaRa), gB gene promoter fragment P or N was cloned. Among the obtained plasmids, a plasmid comprising gB promoter fragment P in a right direction, i.e. in a direction enabling NDV-F protein expression, was referred to as "pKA4BPF" and a plasmid comprising fragment N in a right direction was referred to as "pKA4BNF" (FIG. 3).

Example 4

Determination of NDV-F protein expression by fluorescent antibody method

FA was conducted as described in Preparation, and as a result, both pKA4BPF and pKA4BNF were proved to express NDV-F protein in CEFs. No distinction in fluorescent intensity was observed between cells where each plasmid was introduced and thus it was estimated that promoter activities of both fragments P and N in CEFs were substantially the same.

Example 5

Preparation of recombinant viruses US10BPF and US10BNF

After each of insertion plasmids pKA4BPF and pKA4BNF constructed in Example 3 was digested with restriction enzyme ScaI to linearize, these plasmids were introduced into CVI988 strain-infected cells as described in Preparation of recombinant virus. The thus obtained recombinant viruses were referred to as "US10BPF" and "US10BNF", respectively. Plaques of the recombinant viruses were stained with anti-F protein monoclonal antibody-DAB (Japanese Patent application No. 4-205933 (Japanese Patent Publication No. 6-22757)). As a result, no significant difference was observed in an expressed amount of F protein by both recombinant viruses and thus it was estimated that the promoter activities of fragments P and N in culture cells were the same.

Figure 4:
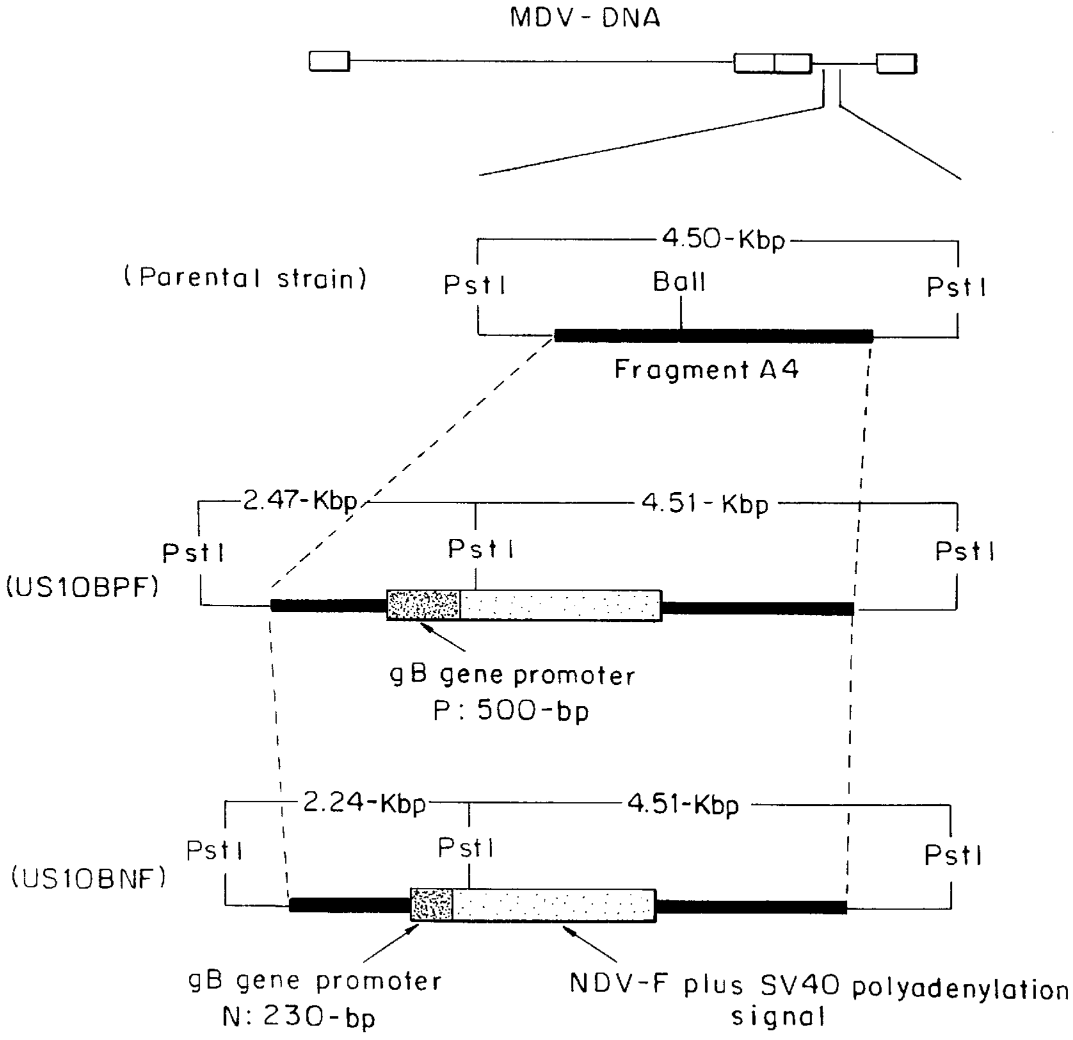
FIG. 4 shows a theoretical scheme of insertion of gB promoters and NDV-F gene for US10BPF and US10BNF as well as a position of fragment A4 used for construction of the insertion vector plasmid.
Figure 5A:
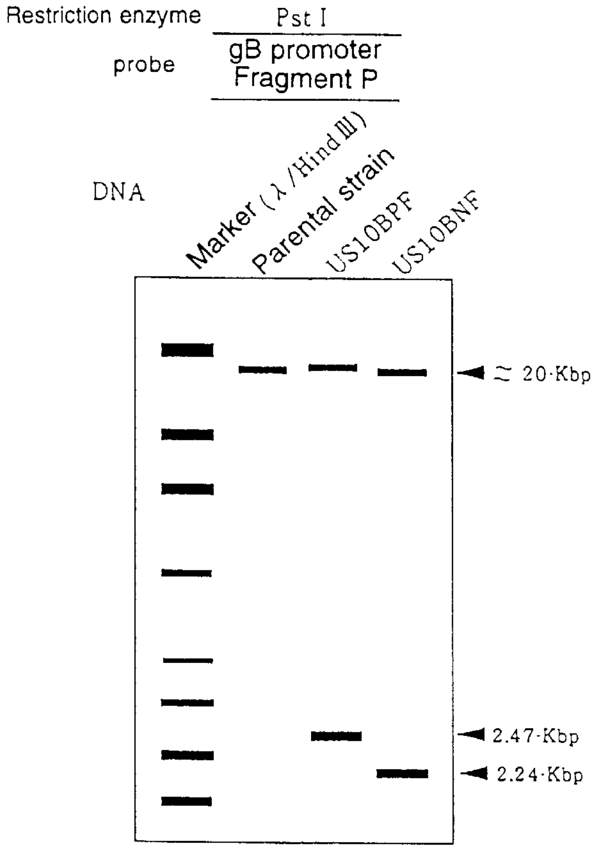
FIG. 5 shows results of Southern hybridization of digestion products with restriction enzyme PstI of DNA extracted from CEFs infected with the recombinant virus US10BPF or US10BNF, using fragment P from gB promoter or fragment A4 as a probe.
Figure 5B:
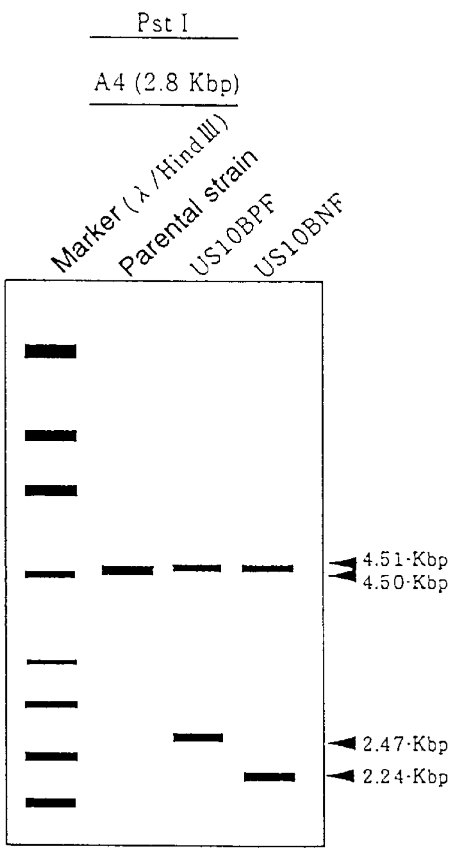

In order to confirm the insertion position of the expression cassette in both recombinant viruses US10BPF and US10BNF, DNAs extracted from infected CEFs were digested with restriction enzymes and then Southern hybridization was conducted. With the use of any of gB promoter fragment P or A4 used as a probe, only those bands as expected were detected to confirm that insertion of the expression cassette was carried out by homologous recombination and that purification of the recombinant viruses surely occurred (FIGS. 4 and 5).

Example 6

Immunization test

In order to prove vaccine effects of the prepared US10BPF and US10BNF against Newcastle disease (ND), chickens of 1 day old were inoculated with these recombinant viruses and challenge test was conducted 6 weeks later. The results are shown in Table 1. US10BLF used herein as one of controls is a recombinant virus wherein expression of F protein is under control of SV40 late promoter which is prepared with insertion plasmid pKA4BF, a construction of which is disclosed in Japanese Patent application No. 4-205933 (Japanese Patent Publication No. 6-22757). This recombinant virus exhibits strong vaccine effects against NDV challenge in SPF chickens but ND protective effects are decreased in chickens having a maternal antibody as shown in Table 1. As shown in Table 1, control chickens and SPF chickens with no inoculation exhibited 0% of protection rate whereas inoculation with US10BPF protected all individuals, even chickens having a maternal antibody, and thus those recombinant viruses where F protein is expressed under control of gB gene promoter exhibited excellent vaccine effects. However, the recombinant virus US10BNF, comprising gB-N promoter, one of gB promoters with half length of gB-P promoter, exhibited no protective effects. Although US10BNF showed F protein expression in culture cells at the same level as that of US10BPF, the protective effects in vivo were much different between US10BPF and US10BNF, which suggested that the use of gB-P region as a promoter is critical for expression of an exogenous gene in recombinant viruses to be administered into the living body.

As to vaccine effects against Marek's disease (MD), as is clear from Table 2, the recombinant virus US10BPF of the present invention was proved to exhibit 90% protection rate against very virulent Marek's disease virus type 1, the protective rate being equivalent to or more than those of the parent strain (non-recombinant), 89%, or commercially available MDV1 vaccine, 84%.

As mentioned above, the recombinant virus US10BPF of the present invention was proved to exhibit strong protection effects against both Newcastle disease (ND) and Marek's disease (MD) viruses and thus to be useful as a polyvalent vaccine.

TABLE 1

| Inoculated virus | Promoter | Protected chickens No./ Challenged chickens No. (protection ratio) |
|---|---|---|
| US10BLF | SV40 late | 14/20 (70%) |
| US10BPF | gB-P | 20/20 (100%) |
| US10BNF | gB-N | 0/20 (0%) |
| No inoculation | — | 0/20 (0%) |

TABLE 2

| Virus | Inoculated amount (PFU) | Tested chickens (No.) | MD onset (No.) | MD Protection ratio (%) |
|---|---|---|---|---|
| US10BPF | 10000 | 20 | 2 | 90% |
| | 1000 | 20 | 6 | 70% |
| *1 | 10000 | 19 | 2 | 89% |
| | 1000 | 20 | 9 | 55% |
| *2 | 1 dose | 19 | 3 | 84% |
| *3 | (—) | 20 | 19 | 5% |

Figure 6:
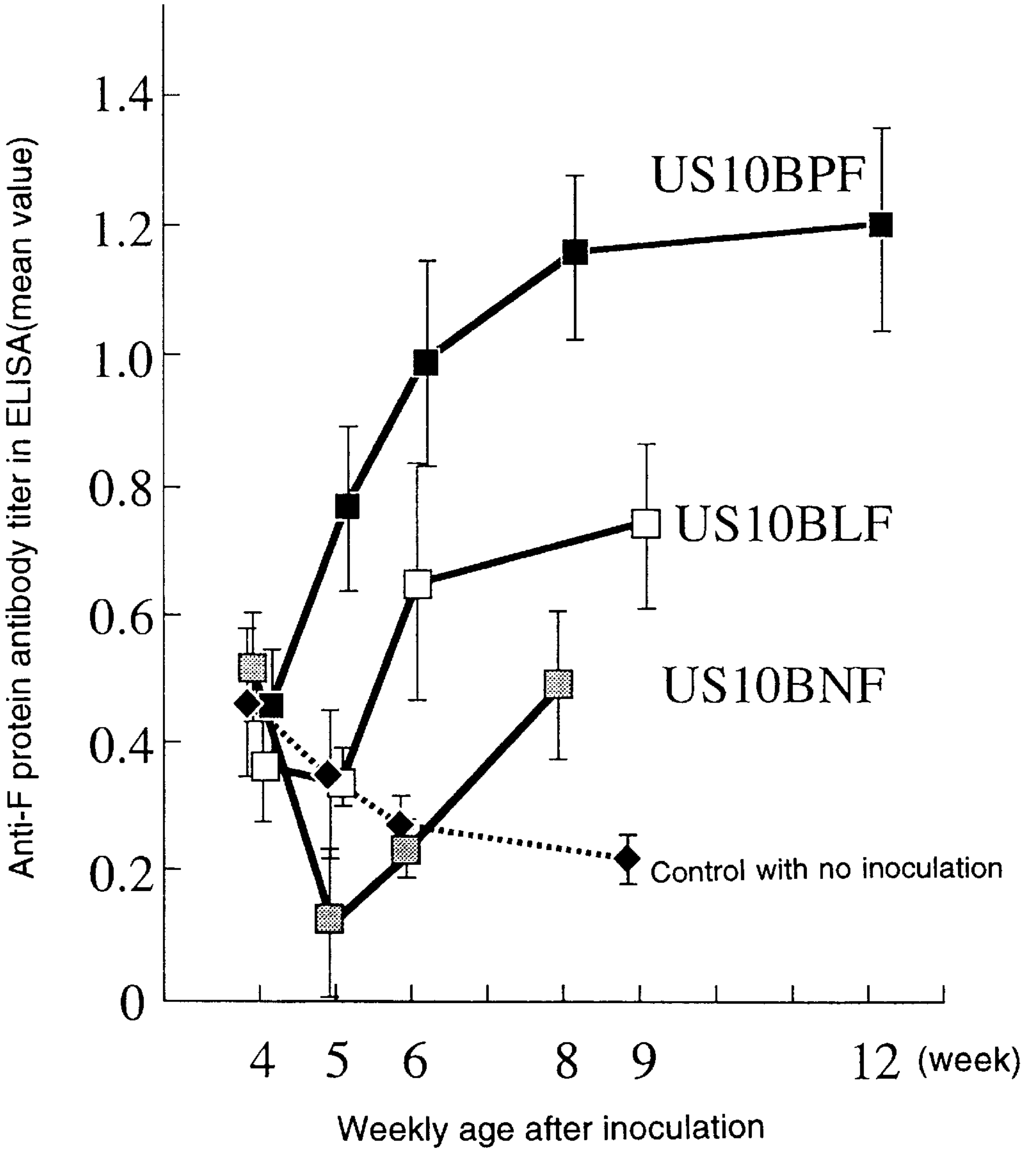
FIG. 6 is a graph showing a change of an anti-F antibody titer in ELISA for chickens inoculated with the recombinant virus US10BPF, US10BNF or US10BLF and chickens without inoculation.

*1: Non-recombinant virus (parent strain)
*2: Commercially available MDV1 vaccine
*3: No immunization A change of anti-F antibody titer in chicken serum as measured by ELISA is shown in FIG. 6. An antibody titer in no inoculation group is of maternal antibodies and was observed to be decreased with the passage of time. In case of US10BLF, it was only after maternal antibodies have decreased to some extent, i.e. at 5th to 6th week, that an anti-F protein antibody titer started to increase. On the other hand, in case of chickens inoculated with US10BPF, an antibody titer increased as soon as at 4th week, and at 6th week when challenge was given, was much higher than that of US10BLF. In this connection, US10BNF showed somewhat increase in an antibody titer at 5th to 6th week but not to such an extent that could protect from Newcastle disease virus challenge, supporting the results of challenge test.

Figure 7:
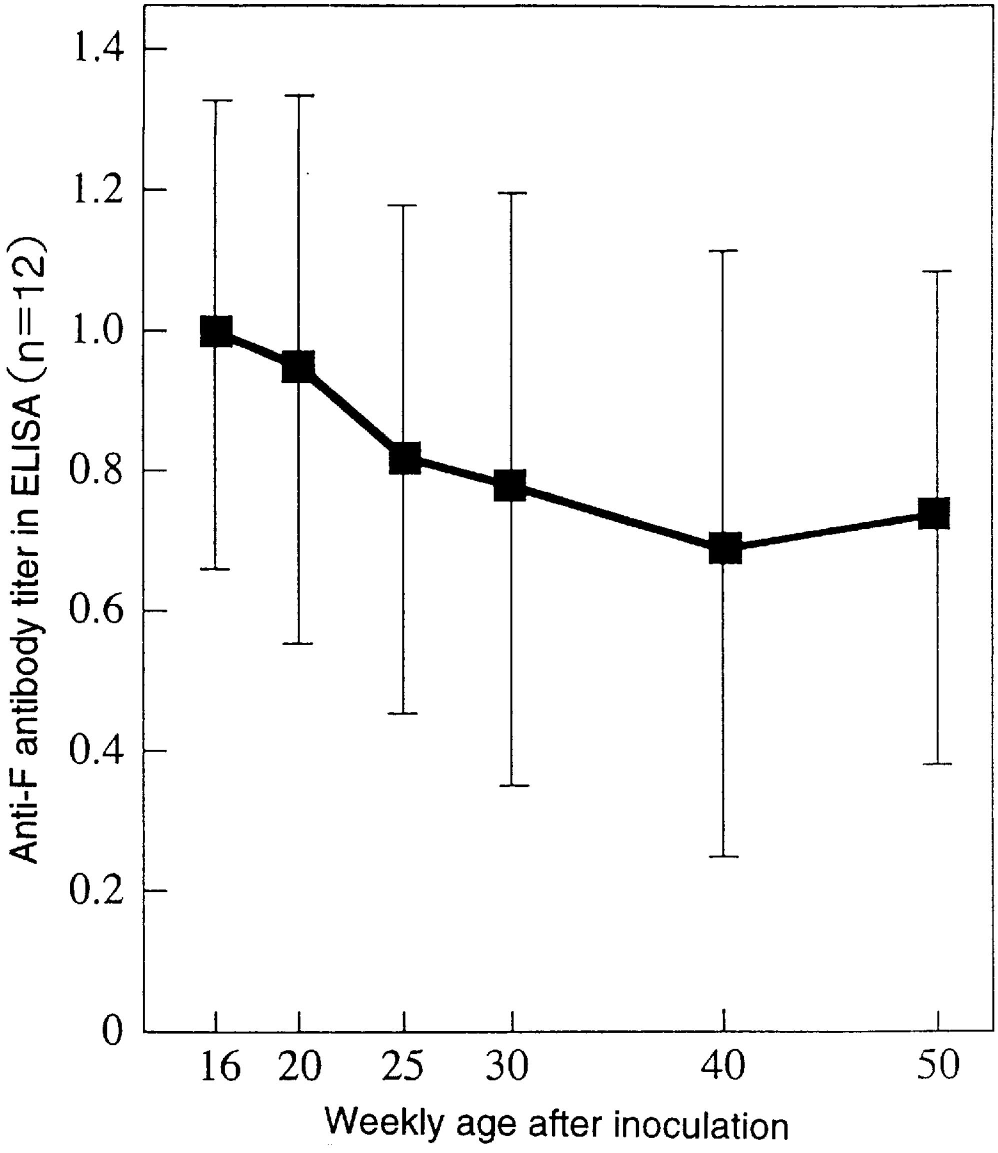
FIG. 7 is a graph showing a change of an anti-F antibody titer in ELISA for chickens inoculated with the recombinant virus US10BPF.

A change of an anti-F antibody titer was observed over a year for chickens inoculated with US10BPF and the results are shown in FIG. 7. An anti-F antibody titer throughout the year exceeded the anti-F antibody titer for the group inoculated with US10BLF, i.e. 0.65 (FIG. 6), which was obtained when it showed 70% protection ratio (Table 1) in challenge test with Newcastle disease virus, indicating that in most of the individuals the vaccine effects of the recombinant virus continue to be effective for at least one year.

Virus was recovered at 7th week after inoculation and the results are shown in Table 3. US10BLF showed 0/5(+), i.e. no viral recovery, whereas US10BPF was 5/5(+), i.e. high viremia, suggesting that US10BPF exhibits excellent propagation in vivo. Furthermore, all the plaques of recovered recombinant virus were proved to express F protein, confirming that the recombinant virus of the present invention is genetically stable even in vivo and infects persistently. This demonstrates that the virus vector system of the present invention is not merely a transient expression system but persistently infects even in the presence of a maternal antibody and thus can be quite useful as a drug delivery system (DDS) for efficiently producing an exogenous gene product within the living body. Accordingly, the system of the present invention is not only a vector for administration of vaccine but also DDS being quite useful for delivery of such substances as required to be supplied for a long period of time within the living body such as hormones or cytokines.

TABLE 3

| | | | Viral recovery | |
|---|---|---|---|---|
| Inoculated virus | Promoter | Chicken No. | Recovery | Ratio of recombinant virus |
| US10BLF | SV40 late | 61 | — | |
| | | 62 | — | |
| | | 63 | — | |
| | | 64 | — | |
| | | 65 | — | |
| US10BPF | gB-P | 51 | + | 69/69 |
| | | 52 | + | 47/47 |
| | | 53 | + | 22/22 |
| | | 54 | + | 9/9 |
| | | 55 | + | 48/48 |

What is claimed is:

1. A recombinant Marek's disease virus (MDV), which is genetically stable in vivo and able to persistently infect a host, having a gene expression cassette incorporated in a non-essential region of the genome, wherein the gene expression cassette contains an exogenous gene operatively linked to an MDV gB promoter; wherein the MDV gB promoter comprises the sequence of about 61 to 557 nucleotides upstream of the gB coding sequence endogenous to the MDV, and the exogenous gene encodes a hormone, a cytokine, or a vaccine antigen effective for prevention of chicken virus infectious diseases.

2. The recombinant Marek's disease virus (MDV) according to claim 1, wherein said promoter comprises nucleotides 61 to 557 of SEQ ID NO: 1.

3. The recombinant Marek's disease virus (MDV) according to claim 1, wherein said promoter consists of nucleotides 61 to 557 of SEQ ID NO:1.

4. The recombinant Marek's disease virus (MDV) of claim 1 wherein said exogenous gene encodes a vaccine antigen effective for prevention of chicken viral infectious disease.

5. The recombinant Marek's disease virus (MDV) of claim 1 wherein said exogenous gene encodes a hormone or a cytokine.

6. A live vaccine for animal which comprises the recombinant herpes virus of claim 1.

7. A polyvalent live vaccine for animal which comprises the recombinant herpes virus of claim 1.

8. The vaccine of claim 6 wherein the animal is chicken.

* * * * *